United States Patent [19]

Murakami et al.

[11] 4,290,306
[45] Sep. 22, 1981

[54] METHOD AND APPARATUS FOR PROBING INTO A REFINING FURNACE OR THE LIKE FOR TEMPERATURE MEASUREMENT FOR SAMPLING, OR FOR BOTH

[75] Inventors: Keikichi Murakami; Hideo Kaneko, both of Kobe, Japan

[73] Assignee: Kawasaki Jukogyo Kabushiki Kaisha, Kobe, Japan

[21] Appl. No.: 126,105

[22] Filed: Feb. 29, 1980

[30] Foreign Application Priority Data

Mar. 5, 1979 [JP] Japan .................................. 54/25785
Mar. 20, 1979 [JP] Japan .................................. 54/32520

[51] Int. Cl.³ .............................................. G01N 1/12
[52] U.S. Cl. .................................... 73/354; 73/863.85
[58] Field of Search .......... 73/421 B, 422 R, 422 TC, 73/423 R, 343 B; 222/603, 629

[56] References Cited

U.S. PATENT DOCUMENTS

| 2,516,097 | 7/1950 | Woodham | 73/421 B |
| 3,572,124 | 3/1971 | Nagaoka | 73/354 |
| 3,581,948 | 6/1971 | Detalle | 222/603 |
| 3,598,380 | 8/1971 | Jilek | 73/343 B |

FOREIGN PATENT DOCUMENTS

345371 11/1972 U.S.S.R. .......................... 73/343 B

Primary Examiner—S. Clement Swisher
Attorney, Agent, or Firm—Haseltine and Lake

[57] ABSTRACT

For sampling, and/or measuring the temperature of, the molten metal within a furnace such as a steel converter, a probe is inserted into the furnace through an opening formed at or in the adjacency of its bottom. An inert gas, either singly or in combination with oxygen and a hydrocarbon gas such as propane, butane, and natural gas, is constantly blown into the furnace through the opening in order to prevent the influx of the molten metal.

23 Claims, 12 Drawing Figures

METHOD AND APPARATUS FOR PROBING INTO A REFINING FURNACE OR THE LIKE FOR TEMPERATURE MEASUREMENT FOR SAMPLING, OR FOR BOTH

BACKGROUND OF THE INVENTION

This invention relates to the art of probing into a vessel containing a high-temperature fluid material, as for sampling, and/or measuring the temperature of, the fluid material. The invention has particular utility in conjunction with steel converters and other refining furnaces including degassing furnaces, electric furnaces, and mixers, as well as ladles for use with such furnaces. In these applications, therefore, the invention pertains to the art of probing the molten metal bath for the noted purposes.

Steelmakers have usually resorted to the use of a secondary lance (sublance), in addition to the primary oxygen lance, in probing into a converter for the temperature measurement, and/or sampling, of the bath. The use of the sublance gives rise to serveral inconveniences and difficulties. First of all, since the sublance is inserted into the converter from above and is of considerable length, it requires a large space over the converter.

Another difficulty is encountered when, as has frequently been the case, the iron or slag within the converter adheres excessively to the sublance. Such iron or slag adhesion to the sublance may even make it impossible to withdraw the sublance from the converter through its mouth hood, thus demanding a rest in the converter operation. The stripping the iron or slag from the sublance is also a difficult and time-consuming job.

A further inconvenience arises from the fact that the sublance must be inserted into the converter in a position offset from the converter axis, so as not to interfere with the oxygen lance extending along the converter axis. Thus the sublance receives greater heat from the center side of the converter than from its wall side. Inevitably undergoing thermal deformation, therefore, the sublance is usually bent toward the center of the converter.

SUMMARY OF THE INVENTION

The present invention provides an improved method of, and apparatus for, probing into a vessel containing a high-temperature fluid material, for such purposes as sampling, and/or ascertaining the temperature of, the fluid material. In essence, the invention contemplates the insertion of a probe, having means for performing the desired purposes, into the vessel through an opening formed at or in the vicinity of its bottom. The inflow of the fluid material into the probe entrance opening is avoided by constantly blowing a gas or gases, normally an inert gas, under pressure into the vessel therethrough.

According to the method and apparatus of this invention summarized in the foregoing, the probe requires a minimal stroke for moving into and out of the vessel because the probe can immediately reach the fluid material on entering the vessel. In preferred embodiments disclosed herein, therefore, the probe is mounted directly on the piston rod of a fluid actuated cylinder and is thereby carried into and out of the vessel. The compact probing apparatus according to the invention can thus be advantageously substituted for the inconveniently elongated sublance employed heretofore.

Since the probe is usually inserted upwardly into the vessel, either vertically or at an angle to the perpendicular, the invention also contemplates the provision of a novel probe construction. In the preferred embodiments, in which the invention is adapted for use with a steel converter, the probe comprises a housing, a sample container within the housing for receiving a sample quantity of the molten metal within the converter, a first pyrometer for measuring the temperature of the bath within the converter, and a second pyrometer for measuring the temperature of the metal sample within the sample container. Disposed at the bottom end of the sample container, the second pyrometer is effective for quickly detecting the solidifying temperature of the metal sample.

An additional feature of the novel probe resides in an annular bulge formed circumferentially on its housing, below the inlet for admitting the sample metal into the sample container. When the probe is inserted into the converter, the annular bulge on its housing serves to divert the gas stream away from the upper portion of the probe, thereby permitting smooth inflow of the molten metal into the sample container and further enabling the first pyrometer to detect the bath temperature without being affected by the gas stream.

According to a further aspect of the invention, the probing apparatus additionally comprises a tubular entryway structure extending outwardly from the probe entrance opening and defining therein a rectilinear entryway for the insertion of the probe, and the delivery of the pressurized gas, into the converter therethrough. The probe on the piston rod of the cylinder is normally enclosed in an open-ended tubular sheath which is rigidly coupled at one end to the cylinder in coaxial relationship thereto and which is adapted for end-to-end, detachable engagement with the entryway structure.

The probing apparatus further comprises means acting on the cylinder for moving the sheath into and out of detachable engagement with the entryway structure, and means for aligning the axis of the cylinder with the axis of the entryway structure. All such means are effectively integrated for efficient probing operation into steel converters or the like in the usual plant environment.

The above and other features and advantages of this invention will become more apparent from a study of the following detailed disclosure in which reference is directed to the attached drawings.

DETAILED DESCRIPTION OF THE INVENTION

Figure 1:
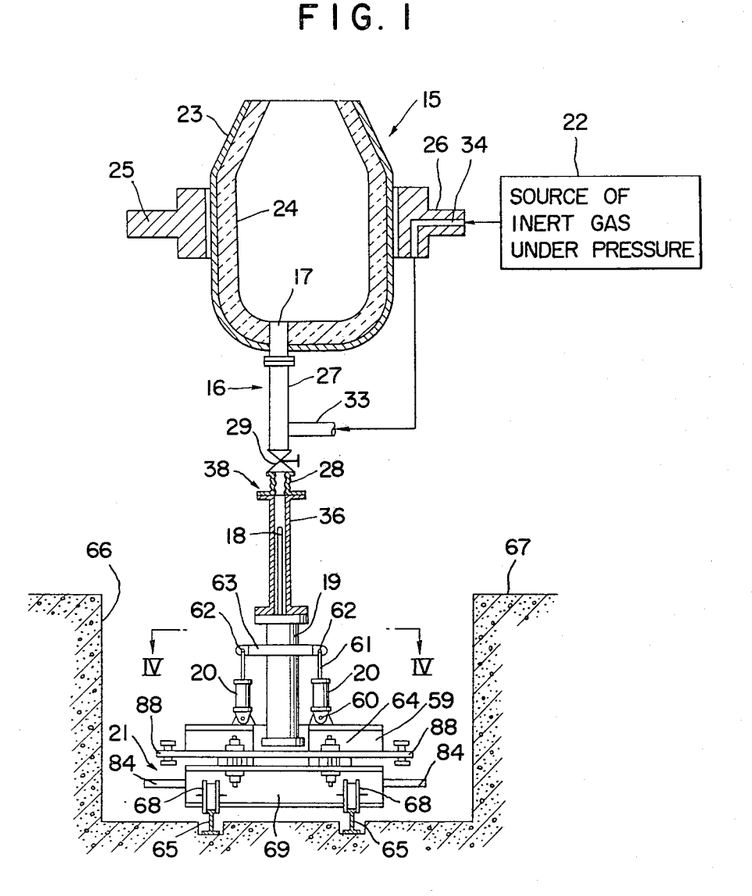
FIG. 1 is a schematic elevation, partly in vertical section of a preferred form of the probing apparatus according to the invention, the apparatus being shown together with, and as adapted for, a steel converter.

FIG. 1 represents one specific adaptation of the present invention, that is, for both measuring the temperature of, and sampling, the molten iron being processed in a steelmaking converter. The principal parts or components of the arrangement shown in FIG. 1 are:

1. a steel converter or vessel 15 in which iron is thermochemically processed or refined into steel;

2. a generally tubular entryway structure 16 extending downwardly from a probe entrance opening 17 formed in the bottom of the converter 15;

3. a probe 18 which houses means for temperature measurement and the sampling of the bath within the converter 15 and which is to be moved linearly into and out of the converter through the entryway structure 16;

4. a fluid actuated cylinder 19 (hereinafter referred to as the probe cylinder) for moving the probe 18 into and out of the converter 15;

5. a plurality of fluid-actuated piston-cylinder actuators 20 (hereinafter referred to as the lift cylinders) for imparting up-and-down motion to the probe cylinder 19, 6. a probe aligning mechanism 21 for aligning the axis of the probe cylinder 19, and therefore of the probe 18, with the axis of the entry-way structure 16 preparatory to the insertion of the probe into the converter 15; and 7. a source 22 of an inert gas under pressure communicating with the entryway structure 16 for delivering the pressurized inert gas into the converter 15 through the probe entrance opening 17 in order to prevent the influx of the molten metal therein.

The converter 15 can be of familiar design comprising a steel shell 23 having a lining 24 of refractory material on its inside surface. A pair of trunnions 25 and 26 on the shell 23 permits the converter 15 to be tilted about a horizontal axis.

Figure 2:
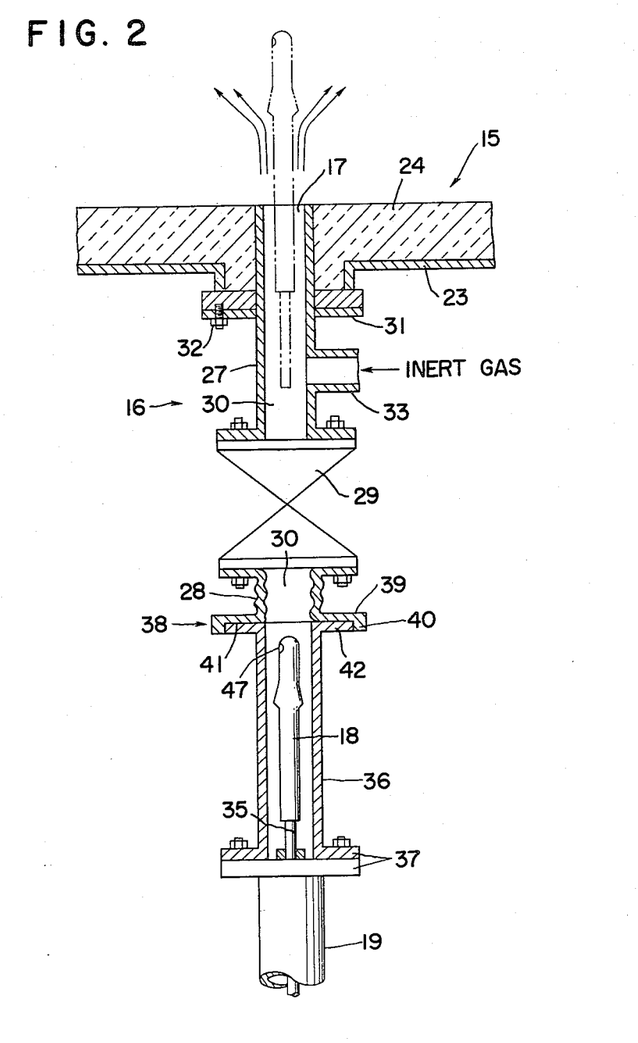
FIG. 2 is a relatively enlarged elevation, in vertical section, showing in particular the details of an entryway structure through which a probe is inserted into the converter in the apparatus of FIG. 1.

FIG. 2 is an enlarged detail view of the entryway structure 16, the probe 18, and the probe cylinder 19. The entryway structure 16 comprises a rigid tube or pipe 27 directly communicating with the probe entrance opening 17 in the bottom of the converter 15 and extending vertically downwardly therefrom, and a short, flexible tube 28 in coaxial relationship with the rigid tube 27. A valve 29 is interposed between rigid tube 27 and flexible tube 28 for the open-shut control of communication therebetween.

The rigid tube 27 and the flexible tube 28 define in combination a rectilinear entryway 30 which leads to the probe entrance opening 17 and which can be opened and closed by the open-shut valve 29. This open-shut valve can take the form of a gate valve, such that the probe 18 can pass through the entryway 30 to or from the probe entrance opening 17 when the valve is opened. The gate valve is shown schematically because of its common, well-known nature. The rigid tube 27 has a flange 31 formed integrally thereon intermediate between its ends for connection to the converter 15 as by bolts or screws 32.

Communicatively coupled to the rigid tube 27 in right angular relationship is a gas supply pipe 33 for delivering the inert gas under pressure from its source 22 (FIG. 1) into the converter 15. The gas supply pipe 33 is in communication with the pressurized gas source 22 through a passageway 34 formed in the converter trunnion 26. The pressurized gas must serve to block the probe entrance opening 17 against bath influx, so that the gas is constantly forced into the converter 15 during its operation, under a pressure of, say, 0.5 to 5.0 kilograms per square centimeter.

In this particular embodiment of this invention, the gas thus delivered into the converter 15 is an inert gas, such as argon or nitrogen, that will not affect the composition of the bath to even the slightest degree. More will be said presently about the use of the gas.

FIG. 2 further shows that the probe 18 is mounted directly on the piston rod 35 of the probe cylinder 19, which is of the double acting type. When the probe cylinder 19 is contracted, the probe 18 is completely enclosed with substantial clearance in a tubular, openended sheath 36 which is coaxially and rigidly coupled at its bottom end to the probe cylinder by a flange union 37. At its top end the sheath 36 makes a detachable, but practically gastight, connection with the bottom end of the entryway structure 16 through a socket-and-flange joint 38.

The socket-and-flange joint 38 comprises a flange 39 formed at the bottom end of the flexible tube 28 and having an annular, downturned rim 40 to define a socket 41, and a flange 42 formed at the top end of the sheath 36 to fit into the socket 41. Thus, upon extension of the noted lift cylinders 20 (FIG. 1), the sheath flange 42 becomes engaged in the socket 41 thereby establishing the gastight connection between entryway structure 16 and sheath 36. The sheath flange 42 readily disengages from the socket 41 upon contraction of the lift cylinders 20.

Figures 3, 4:
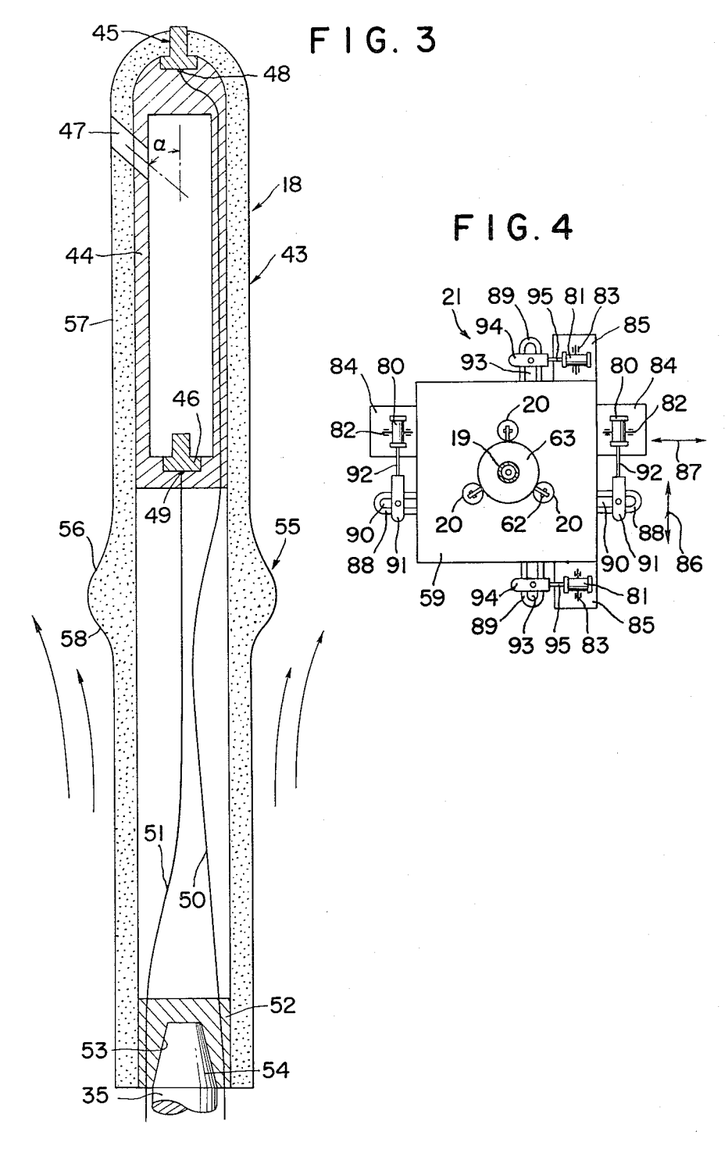
FIG. 3 is a still further enlarged eleration, in axial section, of the probe used in the apparatus of FIG. 1.
FIG. 4 is a horizontal sectional view taken along the line IV—IV of FIG. 1 and showing, in a top plan view, a cylinder aligning mechanism in particular.

FIG. 3 reveals the internal makeup of the probe 18 to be plunged into the converter bath by the probe cylinder 19. The probe comprises:

1. a laminated paper housing 43 of generally tubular shape;

2. a sample container 44, also of generally tubular shape, accommodated within the housing 43 adjacent its top end:

3. a first thermoelectric pyrometer 45 buried in the top end of the housing 43 and the sample container 44; and 4. a second thermoelectric pyrometer 46 at the bottom end of the sample container 44.

A sample inlet 47 is formed through the housing 43 and the container 44, in the vicinity of their top ends, to admit the molten metal into the interior of the container. The sample inlet 47 slopes upward as it extends radially outwardly of the container 44 and the housing 43. The angle $\alpha$ between the intersecting axes of the probe 18 and the sample inlet 47 should be determined so as to facilitate the inflow of the molten metal into the sample container 44 and also to permit ready escape of the air therefrom.

The first thermoelectric pyrometer 45 has a builtin thermocouple 48 which operates on the well known principle for measuring the temperature of the bath in the converter 15. The second thermoelectric pyrometer 46 also has a built-in thermocouple 49 for measuring the temperature of the metal sample within the sample container 44. The leads 50 and 51 of the respective thermocouples 48 and 49 extend downwardly through the probe 18 and pass out of same through a plug 52 closing the open end of the housing 43. The plug 52 has formed therein a hole 53 snugly receiving the top end 54 of the probe cylinder piston rod 35.

Further, the probe 18 features an annular bulge 55 formed circumferentially on the housing 43 intermediate its opposite ends. It is essential that the bulge 55 lie below the sample inlet 47. As will be better understood by referring back to FIG. 2, the annular bulge 55 functions, when the probe 18 is inserted into the converter 15, to divert away from the upper portion of the probe the rising stream of the inert gas being constantly forced into the container, as indicated by the arrows. Thus the rising gas stream will not interfere with the influx of the molten metal into the probe 18 through the sample inlet 47, nor will it hamper the accurate measurement of bath temperature by the first thermoelectric pyrometer 45.

Perferably the upper side 56 of the annular bulge 55 forms a continuous, smoothly curved surface with the outer surface 57 of the probe housing 43, as drawn. Such a curved surface serves to minimize the attachment, and consequent solidification, of the molten metal thereto while the probe 18 is inserted into the converter 15. The lower side 58 of the annular bulge 55 also forms a continuous, curved surface with the outer surface 57 of the probe housing 43, in order to effectively divert the gas stream in the above described manner.

With reference to both FIGS. 1 and 4, the three lift cylinders 20, of the double acting type, are mounted uprightly on a generally square, boxlike slide 59, with their head ends pivotally supported at 60 on the slide. The lift cylinders 20 are disposed at equal angular spacings about the axis of the probe cylinder 19. The piston rods 61 of the lift cylinders 20 are pivotally pinned at 62 to a support flange 63 integrally and coaxially mounted on the probe cylinder 19.

Thus, with the simultaneous extension and contraction of these lift cylinders 20, the probe cylinder 19 and the sheath 36 thereon move up and down, into and out of engagement with the entryway structure 16 via the socket-and-flange joint 38. Further, the lift cylinders 20 permit extension and contraction individually, for adjusting the angle of the axis of the probe cylinder 19 with respect to the perpendicular. Such functions of the lift cylinders 20 will become better understood when considered in light of the subsequent description of the probe aligning mechanism 21.

The slide 59 is mounted on a base or carriage 69 by several coupling means 64 to be detailed later. The coupling means 64 permit the slide 59 to travel within limits in any direction in a horizontal plane relative to the base 69. In this particular embodiment the base 69 takes the form of a wheeled carriage capable of rolling along a pair of rails 65 laid over the bottom of a trench 66 formed in a steelmaking plant floor 67. Originally intended for use with usual ladle cars, the trench 66 with the railing 65 extends horizontally in right angular relationship to the aligned axes of the converter trunnions 25 and 26.

The carriage 69 has wheels 68 in rolling engagement with the rails 65, for traveling therealong together with the various means mounted thereon. The wheeled carriage 69 is brought under the converter 15 as required and locked against movement by suitable means (not shown) during the operation of bath temperature measurement or sampling or both. The probe aligning mechanism 21 acts between slide 59 and carriage 69 for horizontally moving the probe cylinder 19 into axial alignment with the entryway structure 16. Prior to the discussion of the probe aligning mechanism 21, however, the coupling means 64 slidably connecting the slide 59 to the carriage 69 will be explained in connection with their detail view given in FIG. 5.

Figure 5:
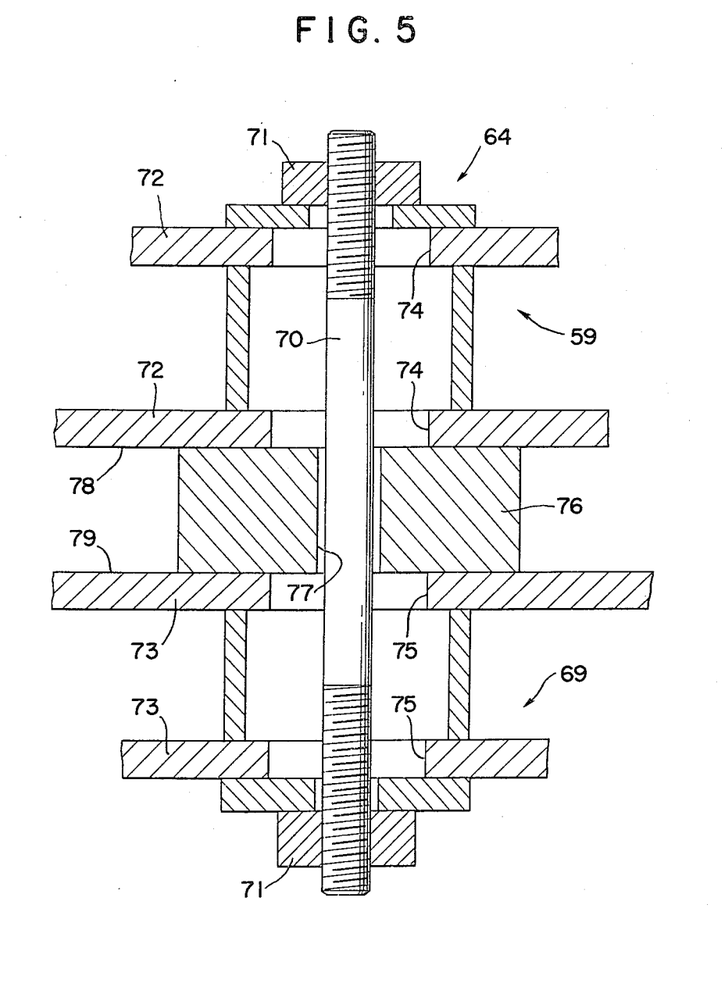
FIG. 5 is an enlarged, fragmentary elevation, in vertical section showing one of several coupling means interconnecting a slide and a base for relative sliding motion in horizontal planes in the apparatus of FIG. 1.

Each coupling means 64 includes a tap end stud 70, with nuts 71 on its opposite ends, fastening together the bottom of the slide 59 and the top of the carriage 69. The bottom of the slide 59 is composed of two parallel spaced plates 72, and the top of the carriage 69 is likewise composed of two parallel spaced plates 73. The slide bottom plates 72 and the carriage top plates 73 have formed therein clearance holes 74 and 75 of equal diameter, through which extends the tap end stud 70 with considerable clearance.

A spacer 76, with a hole 77 formed centrally therein, is sleeved upon the tap end stud 70 to provide a spacing between slide 59 and carriage 69. At least parts of the lower surface 78 of the slide bottom lower plate 72, and of the upper surface 79 of the carriage top upper plate 73, have a smooth finish for sliding contact with the spacer 76 with as little frictional resistance as possible.

It is thus seen that the coupling means 64 permit the slide 59 and the carriage 69 to slide relative to each other in their contiguous horizontal planes within the limits imposed by the clearances with which the studs 70 pass through the holes 74 and 75. The tightening torques of the nuts 71 on the studs 70 should be such as to permit such relative sliding motion of the slide 59 and the carriage 69, while preventing the vertical displacement of the slide away from the carriage.

Reference is now directed to both FIGS. 1 and 4 in order to describe the configuration of the probe aligning mechanism 21. This mechanism includes a pair of fluid-actuated piston-cylinder actuators 80 (hereinafter referred to as the align cylinders) and another pair of similar align cylinders 81, both of the double acting type. These align cylinders 80 and 81 are pivotally supported at 82 and 83 on respective brackets 84 and 85 projecting outwardly from the four sides of the carriage 69. The first pair of align cylinders 80, on the brackets 84 on the opposite sides of the carriage 69, each extend in a first horizontal direction indicated by the arrow 86 in FIG. 4. Mounted on the other brackets 85 on the opposite sides of the carriage 69, the second pair of align cylinders 81 each extend in a second horizontal direction 87 which is at right angles to the first direction 86.

The probe aligning mechanism 21 further comprises first and second pairs of opposed U-shaped coupling members 88 and 89 projecting horizontally from the four sides of the slide 59. The first pair of coupling members 88 have formed therein slots 90 extending in the second direction 87 for operative engagement with complementary coupling members 91 on the tips of the piston rods 92 of the first pair of align cylinders 80. The slotted coupling members 88 make positive engagement with the complementary coupling members 91 in the first direction 86 and make sliding engagement therewith in the second direction 87.

The second pair of coupling members 89 have formed therein slots 93, elongated in the first direction 86, for operative engagement with complementary coupling members 94 on the tips of the piston rods 95 of the second pair of align cylinders 81. The slotted coupling members 89 make positive engagement with the complementary coupling members 94 in the second direction 87 and make sliding engagement therewith in the first direction 86.

Such being the organization of the probe aligning mechanism 21, the slide 59 travels in the first direction 86 relative to the wheeled carriage 89 upon extension or contraction of the first pair of align cylinders 80, and in the second direction 87 upon extension or contraction of the second pair of align cylinders 81. Consequently the slide 59 is movable in any direction in the horizontal plane to bring the probe cylinder 19 into axial alignment with the entryway structure 16.

In the operation of the probing apparatus shown in FIGS. 1 through 5, the wheeled carriage 69, together with the probe 18, probe cylinder 19, probe aligning mechanism 21, etc., mounted thereon, is to be rolled along the rails 65 in the trench 66 by suitable drive means (not shown) to the position just under the converter 15 when the temperature of the bath in the converter is to be measured and/or when its sample is to be extracted. In that position the carriage 69 should be suitably locked against movement. It is assumed that the three lift cylinders 20 on the slide 59 are now contracted to hold the probe cylinder 19, and the probe sheath 36 thereon, in the lowermost position. The probe cylinder 19 itself is also assumed to be contracted to hold the probe 18 retracted within the sheath 36.

Following the locking of the wheeled carriage 69 in the position immediately below the converter 15, the two pairs of align cylinders 80 and 81 are extended or contracted, as required, to move the probe cylinder 19, or the probe 18 on its piston rod 35, into axial alignment with the entryway structure 16. Then the lift cylinders 20 on the slide 59 are extended to raise the probe cylinder 19 until the flange 42 of the probe sheath 36 thereon fits closely into the socket 41 defined by the rimmed flange 39 at the bottom end of the entryway structure 16.

The lift cylinders 20 act not only to raise the probe cylinder 19, as above, but also to adjust its attitude as required. An exact axial alignment between the probe cylinder 19 and the entryway structure 16 is not, however, an absolute requirement: the flexible tube 28 at the bottom end of the entryway structure 16 allows some misalignment between the rigid tube 27 and the probe sheath 36.

The open-shut valve 29 is opened after the proper connection of the probe sheath 36 to the entryway structure 16. Then the probe cylinder 19 is extended to insert the probe into the converter 15 through the probe entrance opening 17. The first thermoelectric pyrometer 45 at the tip of the probe 18 measures the temperature of the molten metal within the converter 15. A desired sample quantity of the molten metal flows into the sample container 44 within the probe 18 through the sample inlet 47, and the second thermoelectric pyrometer 46 at the bottom end of the sample container measures the temperature of the sample.

In the steelmaking operation by the converter 15 it is customary to measure the carbon content of the molten metal therein at given instants in time and to correspondingly control its operating conditions. The carbon content can be ascertained from the solidifying temperature of the bath sample. Within the sample container 44 the solidification of the sample starts from its bottom end and proceeds upward. Disposed at the bottom end of the sample container 44, the second thermoelectric pyrometer 46 can detect the solidifying temerature of the sample as soon as its solidification commences.

The probe cylinder 19 is contracted upon completion of the temperature measuring and sampling operations by the probe 18, thereby causing retraction of the probe back into the sheath 36. Then, after reclosing the on-off valve 29, the lift cylinders 20 are contracted to disconnect the socket-and-flange joint 38. The solidified sample within the sample container 44 is analyzed to determine its composition.

Figure 6:
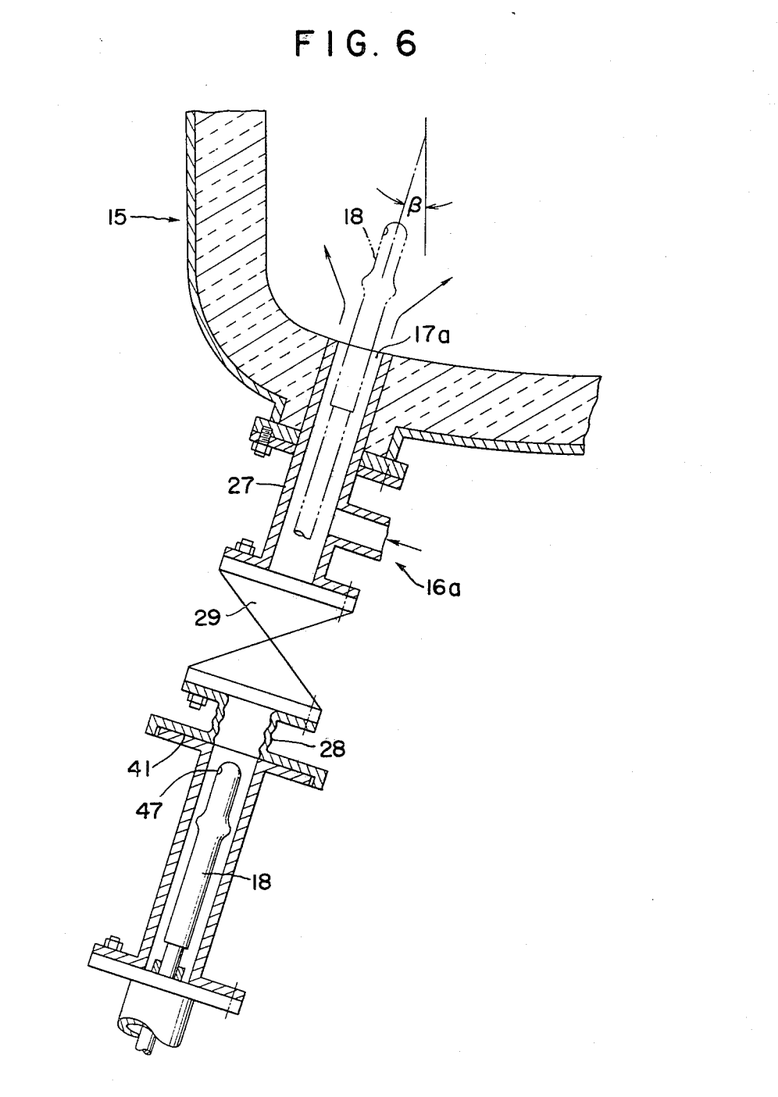
FIG. 6 is a view similar to FIG. 2 but showing a slight modification of the probing apparatus.

Although the entryway structure 16 extends vertically downward from the bottom of the converter in the above embodiment of the invention, such a structure may be disposed at an angle to the perpendicular, as shown at 16a in FIG. 6. The modified entryway structure 16a has its axis oriented at an angle $\beta$ to the perpendicular and is open to a probe entrance opening 17a. Thus, even if the probe entrance opening 17a is considerably offset from the axis of the converter 15, the probe 18 can reach the neighborhood of the converter axis, along which the oxygen lance (not shown) is inserted into the converter.

Figure 7:
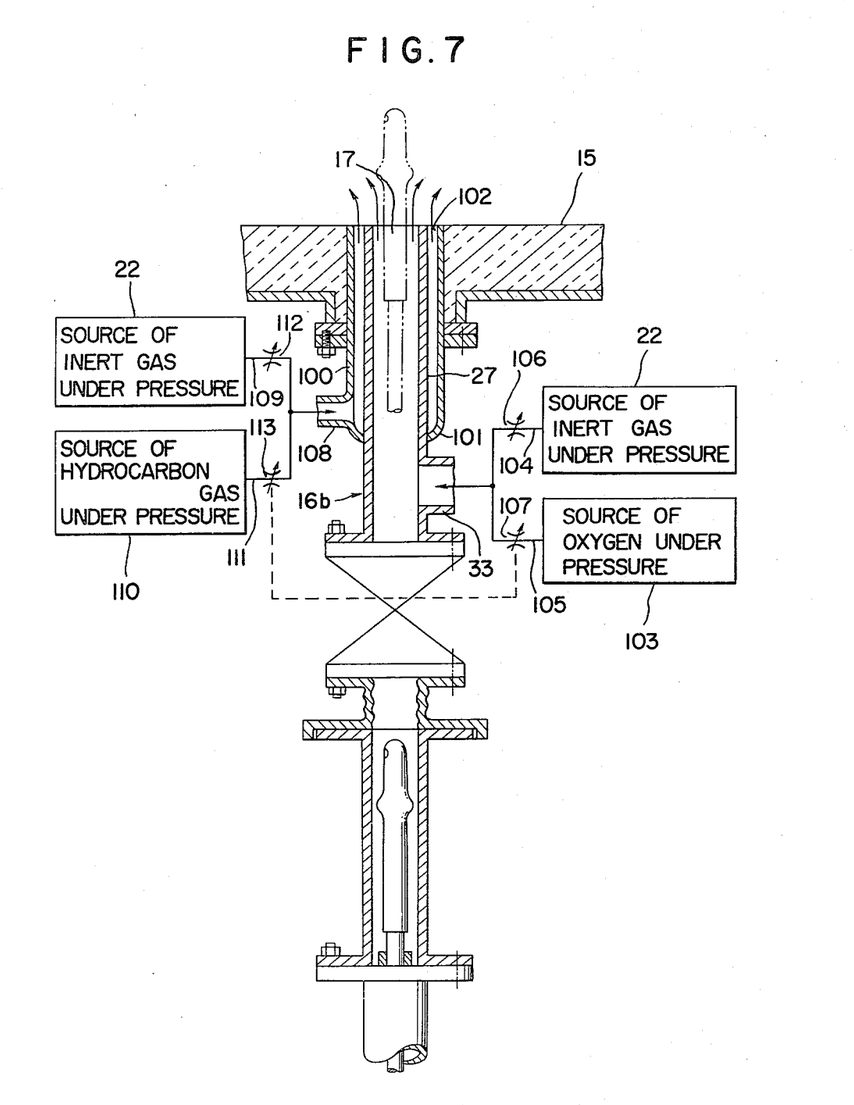
FIG. 7 is also a view similar to FIG. 2 but showing another slight modification of the probing apparatus.

The embodiment of the invention shown in FIGS. 1 through 5 employs argon, nitrogen, or like inert gas for shielding the probe entrance opening from the molten metal. The use of such inert gases may, however, invite a decrease in the bath temperature, adversely affecting the refining operation. FIG. 7 shows another modified embodiment of the invention that provides a solution to this problem.

The embodiment shown in FIG. 7 features a modified entryway structure 16b having a rigid outer tube 100 concentrically surrounding the rigid tube 27 (hereinafter referred to as the inner tube) with a spacing therebetween. The outer tube 100 is closed at its bottom end 101 and open at its top end to a gas inlet 102 formed in the bottom of the converter 15 so as to concentrically surround the probe entrance opening 17.

The gas supply pipe 33 branching off from the inner tube 27 communicates not only with the source 22 of an inert gas under pressure, as in the preceding embodiments of the invention, but also with a source 103 of oxygen under pressure, by way of respective conduits 104 and 105. The conduits 104 and 105 have flow control valves 106 and 107, respectively, for the control of the rates at which the inert gas and oxygen are delivered into the converter 15 through the probe entrance opening 17.

The outer tube 100 also has a gas supply pipe 108 branching off therefrom. The gas supply pipe 108 communicates on one hand with the source 22 of the pressurized inert gas by way of a conduit 109 and, on the other hand, with a source 110 of a pressurized hydrocarbon gas by way of a conduit 111. The conduits 109 and 111 have flow control valves 112 and 113 for regulating the rates of delivery of the inert gas and the hydrocarbon gas into the converter 15 through the gas inlet 102. The control valves 107 and 113 are intercouple, as indicated by the dashed line, in order that when the control valve 107 is opened, the hydrocarbon gas will be introduced into the converter 15 at a rate required in accordance with the rate of delivery of the oxygen into the converter.

In the operation of the FIG. 7 embodiment, all of the control valves 106, 107, 112 and 113 may be opened to introduce into the converter 15 the inert gas and oxygen through the probe entrance opening 17 and the inert gas and hydrocarbon gas through the gas inlet 102. By the term "hydrocarbon gas", as used herein and in the claims appended hereto, is meant propane, butane, natural gas, or the like which, as is well known, is capable of lowering the temperature of the molten iron or steel within the converter 15 when placed in direct contact therewith.

Should oxygen only be delivered into the converter in combination with the inert gas, it would react with the carbon contained in the bath, supporting combustion to such an extent as to inflict damage on those portions of the inner 27 and outer 100 tubes bounding the openings 17 and 102 and on the neighboring portion of the refractory lining. Such combustion will not take place if oxygen is supplied together with any of the listed hydrocarbon gases, the latter being effective to bring about an endothermic reaction that counteracts the combustion. The inert gas, oxygen, and hydrocarbon gas should be introduced into the converter 15 at flow rates and under pressures necessary to prevent the intrusion of the molten metal into the inner 27 and outer 100 tubes.

The simultaneous delivery of the inert gas, oxygen, and hydrocarbon gas into the converter 15 is, however, not a necessity. If desired, the valves 106 and 112 may both be closed, and the valves 107 and 113 may both be opened. Oxygen only is then expelled into the converter 15 from the inner tube 27, and the hydrocarbon gas only is expelled from the outer tube 100. The oxygen and hydrocarbon gas will serve in combination to shield the openings 17 and 102 from the molten metal instead of the inert gas, without causing thermal damage to the parts adjoining the openings. Neither oxygen nor hydrocarbon gas may be introduced, of course, in cases where the constant supply of the inert gas does not appreciably lower the bath temperature.

Figure 8:
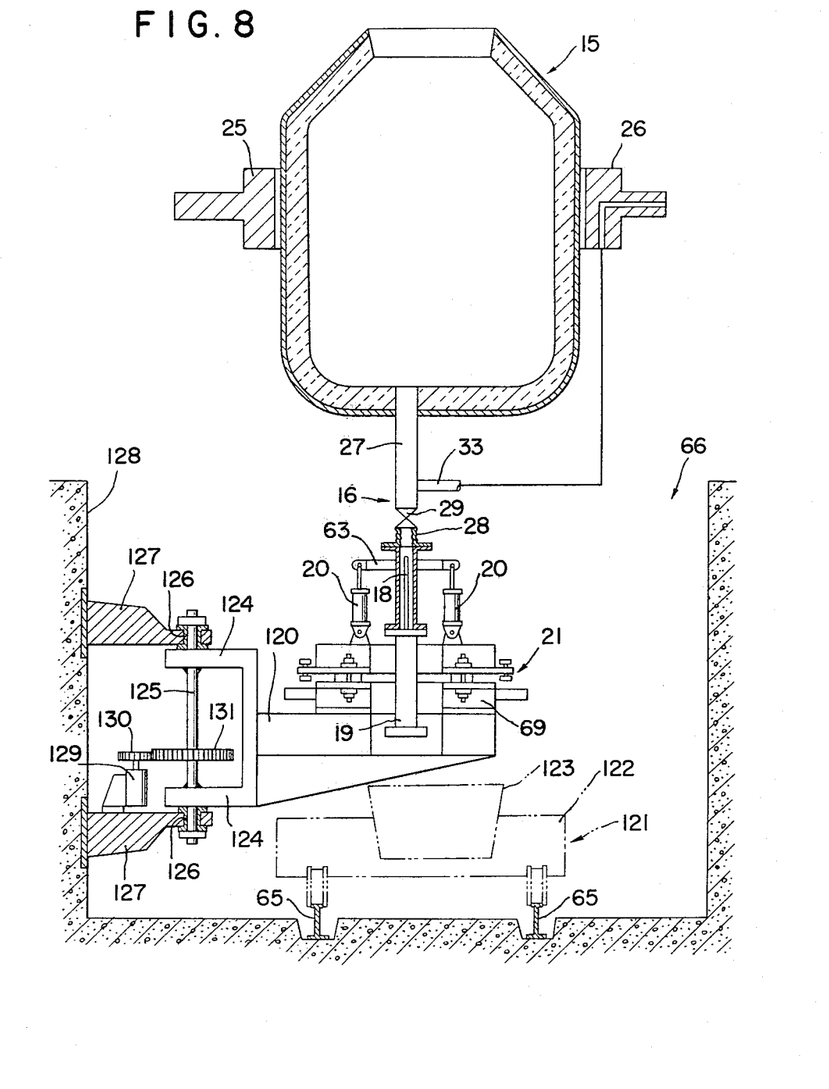
FIG. 8 is a schematic elevation, in vertical section, of another preferred embodiment of the invention.

FIG. 8 shows another preferred embodiment of the invention, which also comprises the entryway structure 16, the probe 18, the probe cylinder 19, the lift cylinders 20, the probe aligning mechanism 21, etc., which are all constructed as in the embodiment of FIGS. 1 through 5. The primary difference is that the base 69 is not wheeled to roll over the rails 65 but is fixedly mounted on a pivoted platform 120. The rails 65 are left for a ladle car 121 including a wheeled carriage 122 carrying a ladle 123, into which the produced steel is to be poured from the converter 15.

The platform 120 is formed to include a clevis or yoke 124 which is nonrotatably coupled to an upstanding, revolving shaft 125. This shaft is rotatably supported, via sleeve bearings 126, by a pair of vertically spaced brackets 127 anchored to a side wall 128 of the trench 66. A motor drive unit 129 on the lower bracket 127 is coupled to a drive pinion 130 in mesh with a driven gear 131 fixedly mounted on the revolving shaft 125.

Normally the probe 18, the probe cylinder 19 and other means on the platform 120 may be held in a retracted position close to the trench wall 128, permitting the ladle car 121 to be moved under the converter 15 for receiving the steel therefrom. For the temperature measurement and/or sampling of the bath in the converter 15, the motor drive unit 129 is set in rotation in a predetermined direction to cause the platform 120 to pivot to the illustrated working position about the axis of the vertical revolving shaft 125. The subsequent procedure of temperature measurement and/or sampling is exactly as set forth above in connection with the embodiment of the invention illustrated in FIGS. 1 through 5.

Figure 9:
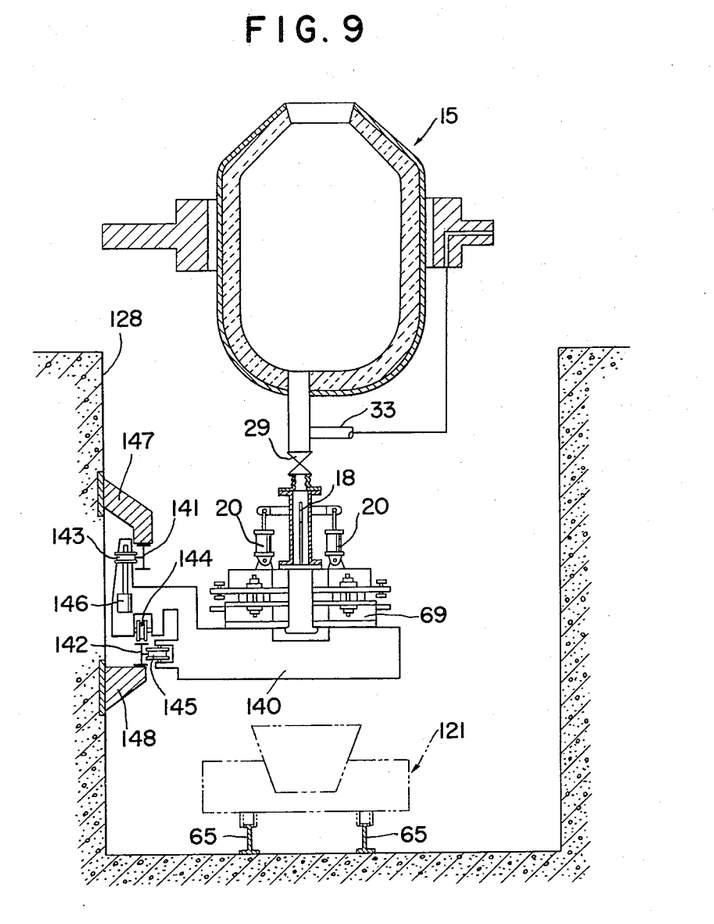
FIG. 9 is a view, similar to FIG. 8, of still another preferred embodiment of the invention.

In a further preferred embodiment of the invention shown in FIG. 9 the base 69 is fixedly mounted on a wheeled carriage 140 capable of running above the ladle car 121 along rails 141 and 142 on the trench wall 128. The carriage 140 has a first set of wheels 143 revolving about vertical axes and making rolling engagement with the upper rail 141, a second set of wheels 144 revolving about horizontal axes and making rolling engagement with the lower rail 142, and a third set of wheels 145 revolving about vertical axes and making rolling engagement with the lower rail 142.

A motor drive unit 146 is coupled directly to one of the first set of wheels 143 for driving the carriage 140 along the rails 141 and 142. These rails are supported by respective supports 147 and 148 projecting from the trench wall 128, and extend alongside the ladle car rails 65.

Thus, as required, the probe 18 together with its actuating and aligning mechanisms is carried to the position just under the converter 15 by the self-propelled carriage 140. The other details of construction and operation will be apparent from the description of the foregoing embodiments.

Figure 10:
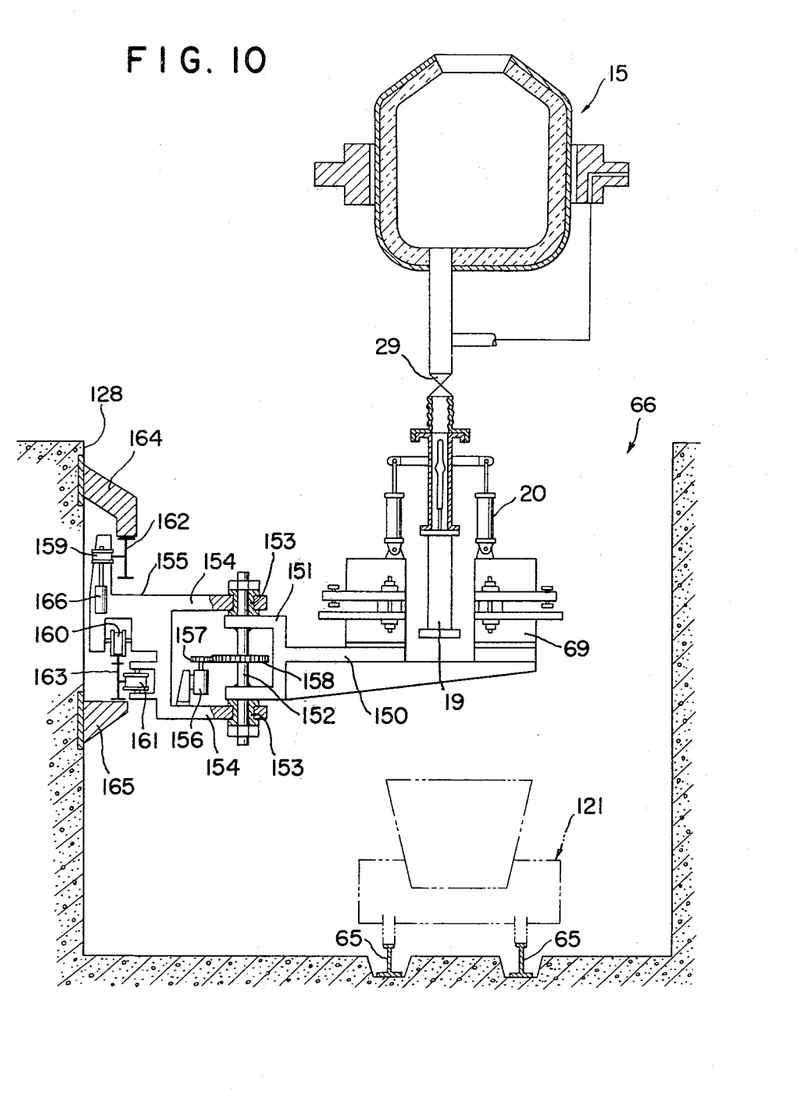
FIG. 10 is a view, also similar to FIG. 8, of a further preferred embodiment of the invention.

A further preferred embodiment of the invention shown in FIG. 10 is, in essence, a combination of the embodiment shown in FIG. 8 and that of FIG. 9. The base 69 is fixedly mounted on a pivotable platform 150. This platform is formed integral with a clevis 151, which is nonrotatably coupled to an upstanding, revolving shaft 152, permitting the platform to pivot about the vertical axis of the shaft. The revolving shaft 152 has its opposite ends journaled in sleeve bearings 153 carried by a pair of vertically spaced arms 154 of a carriage 155.

The lower arm 154 of the carriage 155 has a motor drive unit 156 mounted thereon. The motor drive unit 156 is coupled to a drive pinion 157 in mesh with a driven gear 158 nonrotatably mounted on the revolving shaft 152. Thus the rotation of the motor drive unit 156 results in the pivotal motion of the platform 150 about the axis of the revolving shaft 152.

Just like the carriage 140 of FIG. 9, the carriage 155 has three sets of wheels 159, 160 and 161 in rolling engagement with rails 162 and 163. These rails are mounted on supports 164 and 165 projecting from the trench wall 128 so as to extend alongside the ladle car rails 65. A motor drive unit 166 is coupled to one of the wheels 159 for propelling the carriage 155 along the rails 162 and 163.

When the temperature measurement and/or sampling of the bath in the converter 15 is not desired, the platform 150 together with the means mounted thereon can be pivoted to a retracted position close to the trench wall 128 by motor drive unit 156, so as not to interfere with the travel of the ladle car 121 along the rails 65. As desired or required, moreover, the carriage 155 together with the platform 150 thereon can be moved by the motor drive unit 166 to some other convenient location along the rails 162 and 163.

Figure 11:
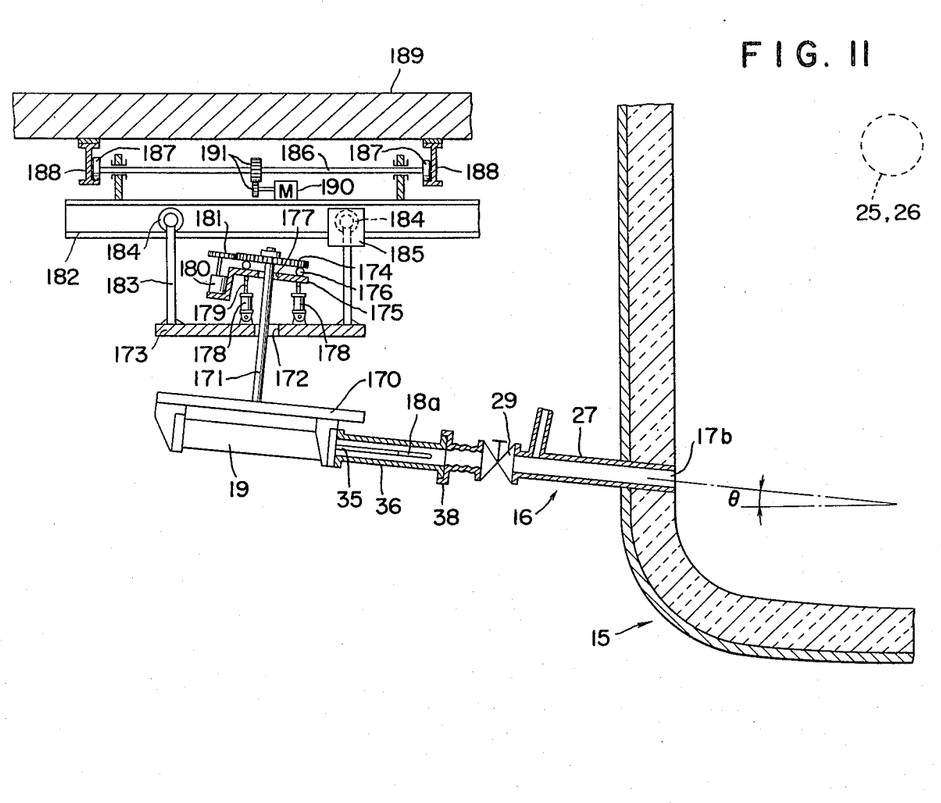
FIG. 11 is an elevation, in vertical section, of a still further preferred embodiment of the invention.

FIG. 11 shows a still further preferred embodiment of the invention, which differs from all of the preceding embodiments in that the probe entrance opening 17b is formed in a side wall of the converter 15, in the vicinity of its bottom. The position of this probe entrance opening 17b is close to the level of the molten metal within the converter but is not reached by the molten metal during normal converter operation.

Undetachably inserted into the probe entrance opening 17b is the entryway structure 16 which may be exactly identical in construction with the structure 16 of, for example, the embodiment shown in FIGS. 1-5. The entryway structure 16 slightly slopes upward as it extends away from the converter 15. The angle θ between the axis of the entryway structure 16 and the plane of the horizon is so determined that a probe 18a, shown in detail in FIG. 12, will reach an appropriate region of the bath. Normally the angle θ may range from 20 to 30 degrees.

Figure 12:
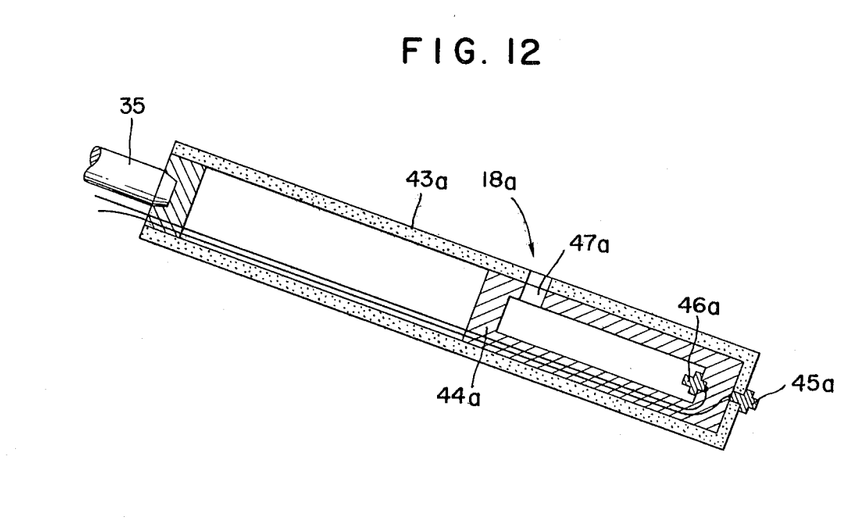
FIG. 12 is an enlarged, axial sectional view of a modified probe for use in the apparatus of FIG. 11.

The modified probe 18a of FIG. 12 has per se been known in the art. It comprises a hollow cylindrical housing 43a accommodating a sample container 44a at its front end. A sample inlet 47a is formed radially through the probe housing 43a and the sample container 44a to admit molten metal into the interior of the container. A first thermoelectric pyrometer 45a is mounted at the extreme front end of the probe housing 43a for temperature measurement of the bath in the converter 15. A second thermoelectric pyrometer 46a is mounted at the front end of the sample container 44a for temperature measurement of the metal sample contained therein.

With reference back to FIG. 11 the probe 18a is ridigly coupled to the piston rod 35 of the probe cylinder 19 and is normally enclosed in the sheath 36 fastened end-to-end to the probe cylinder. The sheath 36 can be connected to and disconnected from the entryway structure 16 via the socket-and-flange joint 38, as in all the foregoing embodiments of the invention.

The probe cylinder 19 is carried by a support 170 rigidly mounted on the bottom end of a revolving shaft 171. This shaft extends upward through a clearance hole 172 formed in a carriage 173. A gear or toothed disc 174 is nonrotatably mounted on the top end of the shaft 171 and rotatably rests on a disc 175 via a suitable bearing 176. The disc 175 has a hole 177 formed centrally therein to permit the shaft 171 to pass therethrough with clearance. The disc 175 is mounted on the carriage 173 via three fluid actuated cylinders 178 disposed at constant angular spacings. Each cylinder 178 is pivotally jointed at its head end to the carriage 173 and is also pivotally jointed at the tip of its piston rod 179 to the disc 175.

The disc 175 carries a motor drive unit 180 which is coupled to a drive pinion 181 in mesh with the driven gear 174. The intermeshing gears 174 and 181 transmit the rotation of the motor drive unit 180 to the shaft 171 thereby causing the probe cylinder 19, probe 18a, etc., to revolve about the axis of the shaft 171.

It will thus be seen that the cylinders 178, the motor drive unit 180, and other means directly associated therewith correspond in combination to the probe aligning mechanism 21 of the FIGS. 1-5 embodiment, since they serve jointly to align the probe 18a with the entryway structure 16. The motor drive unit 180 together with the intermeshing gears 174 and 181 serves the additional purpose, however, of turning the probe cylinder 19, probe 18a and sheath 36 to and away from the axis of the entryway structure 16 about the axis of the revolving shaft 171.

The carriage 173 is suspended from a short, overhead rail 182 by several hanger rods 183 each secured at its bottom end to the carriage and coupled at its top end to a wheel 184 in rolling engagement with the rail. A motor drive unit 185, coupled to one of the wheels 184, propels the carriage 173 along the rail 182 toward and away from the converter 15, for moving the probe sheath 36 into and out of engagement with the entryway structure 16. Thus the wheeled carriage 173 with the motor drive unit 185 corresponds in function to the lift cylinders 20 of the FIGS. 1-5 embodiment.

The rail 182 has rotatably mounted thereon one or more axles 186 terminating at both ends in wheels 187 in rolling engagement with a pair of rails 188. These rails 188 extend at right angles with the first mentioned rail 182 and are shown to be secured to the beams 189 of the plant building. A motor drive unit 190 on the rail 182 is coupled through gearing 191 to the axle 186 for propelling the rail 182 along the rails 188.

When, for example, the converter 15 is to be tilted about the trunnions 25 and 26, the probe 18a, probe cyliner 19 and so forth may be retracted away from the converter along the rail 182 by the motor drive unit 185. Further, the rail 182 itself can be propelled along the pair of rails 188 by the motor drive unit 190 to a position where the probe sheath 36, etc., will not interfere with the tilting motion of the converter 15. The other details of operation will be apparent from the description of the preceding embodiments of the invention. It will of course be understood that the probe entrance opening 17b can be disposed below the level of the molten metal within the converter 15.

Although the method and apparatus of this invention have been illustrated and described as adapted for the steel converter, it is understood that the inventive concepts can find application in probing into other types of vessels containing high-temperature fluid materials in general, for purposes including, but not limited to, the temperature measurement and/or sampling of the fluid materials.

What is claimed is:

1. A method of probing into a vessel containing a high-temperature fluid material, as for measuring the temperature of the fluid material, for sampling the fluid material, or for both purposes, which method comprises:
    (a) forming a probe entrance opening in the vessel in the adjacency of its bottom;
    (b) constantly introducing a gas under pressure into the vessel through the probe entrance opening in order to prevent the influx of the fluid material into the probe entrance opening; and
    (c) inserting a probe into the vessel through the probe entrance opening.

2. The probing method according to claim 1, wherein the gas is an inert gas.

3. The probing method according to claim 2, wherein the inert gas is introduced together with oxygen and a hydrocarbon gas.

4. The probing method according to claim 1, wherein the gas comprises oxygen and a hydrocarbon gas.

5. The probing method according to claim 1, wherein the probe entrance opening is formed in the bottom of the vessel, and wherein the probe is inserted vertically into the vessel.

6. The probing method according to claim 1, wherein the probe entrance opening is formed in the bottom of the vessel, and wherein the probe is inserted at an angle to the perpendicular.

7. The probing method according to claim 1, wherein the probe entrance opening is formed in a side wall of the vessel, and wherein the probe is inserted at an angle to the plane of the horizon.

8. Apparatus for probing into a vessel containing a high-temperature fluid material, as for measuring the temperature of the fluid material, for sampling the fluid material, or for both purposes, the apparatus comprising:
   (a) means defining a probe entrance opening in the vessel in the vicinity of its bottom;
   (b) means for constantly supplying a gas under pressure into the vessel through the probe entrance opening, the pressurized gas being effective to prevent the influx of the fluid material into the probe entrance opening;
   (c) a probe having means for accomplishing a desired probing purpose; and
   (d) means for moving the probe into and out of the vessel through the probe entrance opening.

9. The probing apparatus according to claim 8, wherein the probe is moved substantially vertically into and out of the vessel, and wherein the probe comprises:
   (a) a housing;
   (b) a sample container mounted within the housing;
   (c) there being a sample inlet formed through the housing and the sample container to admit the fluid material into the sample container;
   (d) a first pyrometer mounted at the upper end of the housing for measuring the temperature of the fluid material within the vessel; and
   (e) a second pyrometer mounted at the lower end of the sample container for measuring the temperature of the fluid material within the sample container.

10. The probing apparatus according to claim 9, wherein the housing of the probe has formed thereon an annular bulge located below the sample inlet, the annular bulge being effective, when the probe is inserted into the vessel, to divert away from the upper portion of the probe the gas stream being forced into the vessel.

11. The probing apparatus according to claim 8, further comprising:
   (a) an entryway structure coupled at one end to the vessel and extending outwardly therefrom, the entryway structure defining therein a rectilinear entryway, open to the probe entrance opening, for permitting the probe to be inserted into the vessel therethrough, the entryway further communicating with the gas supplying means for delivering the gas under pressure into the vessel therethrough; and
   (b) an open-shut valve on the entryway structure for preventing the gas from flowing out of the other end of the entryway structure when the probe is not inserted into the vessel, the open-shut valve when opened permitting the probe to pass therethrough.

12. The probing apparatus according to claim 11, wherein the gas is an inert gas, and wherein the apparatus further comprises:
   (a) means defining a gas inlet next to the probe entrance opening in the vessel, the gas inlet also communicating with the inert gas supplying means for introducing the inert gas into the vessel therethrough;
   (b) means for supplying oxygen into the vessel through either of the probe entrance opening and the gas inlet; and
   (c) means for supplying a hydrocarbon gas into the vessel through the other of the probe entrance opening and the gas inlet.

13. The probing apparatus according to claim 11, wherein the probe moving means comprises a fluid-actuated piston-cylinder actuator.

14. The probing apparatus according to claim 13, further comprising an open-ended sheath enclosing the probe and rigidly coupled at one end to the actuator, the other end of the sheath being detachably engaged with said other end of the entryway structure so as to permit the probe to be moved into and out of the vessel by the actuator.

15. The probing apparatus according to claim 14, further comprising:
   (a) means acting on the actuator for moving the sheath into and out of detachable engagement with the entryway structure, and
   (b) means for aligning the axis of the actuator with the axis of the entryway structure.

16. The probing apparatus according to claim 14, further comprising:
   (a) a base;
   (b) a slide slidably mounted on the base for movement in any direction in a plane at right angles with the axis of the entryway structure;
   (c) means for adjustably moving the base in any desired direction in said plane relative to the base; and
   (d) a plurality of second fluid-actuated piston-cylinder actuators each pivotally connected at one end to the slide and at the other end to the first recited actuator for moving the sheath into and out of detachable engagement with the entryway structure.

17. The probing apparatus according to claim 16, wherein the entryway structure extends downwardly from the vessel, and wherein the apparatus further comprises:
   (a) railing extending under the vessel; and
   (b) wheels provided to the base to enable same to roll along the railing.

18. The probing apparatus according to claim 16, further comprising means for supporting the base for pivotal motion about a vertical axis.

19. The probing apparatus according to claim 16, wherein the entryway structure extends downwardly from the vessel, and wherein the apparatus further comprises:
   (a) first railing extending under the vessel;
   (b) second railing extending alongside the first railing; and
   (c) wheels provided to the base to enable same to roll along the second railing.

20. The probing apparatus according to claim 16, further comprising:
   (a) railing said exteriorly of the vessel; and
   (b) a wheeled carriage capable of running along the railing and supporting the base so as to permit its pivotal motion about a vertical axis.

21. The probing apparatus according to claim 14, wherein the entryway structure extends laterally from the vessel, and wherein the apparatus further comprises:
   (a) a shaft rigidly coupled at one end to the actuator and extending upwardly therefrom;

(b) a disc disposed coaxially with the shaft and rotatably supporting same;

(c) a carriage;

(d) a plurality of second fluid-actuated piston-cylinder actuators disposed at constant angular spacings and each pivotally connected at one end to the carriage and at the other end to the disc for aligning the axis of the first recited actuator with the axis of the entry-way structure;

(e) the carriage being movable at least in one direction for moving the sheath into and out of detachable engagement with the entryway structure; and (f) means for imparting rotation to the shaft.

22. The probing apparatus according to claims 15, 16, 17, 18, 19, 20 or 21, wherein the entryway structure includes a flexible portion.

23. The probing apparatus according to claim 22, wherein the flexible portion lies at said other end of the entryway structure, and wherein the sheath and the flexible portion make the detachable engagement with each other through a socket-and-flange joint.

* * * * *